United States Patent
Shipp (12) 
(10) Patent No.: US 6,290,575 B1
(45) Date of Patent: Sep. 18, 2001

(54) SURGICAL LIGATION CLIP WITH INCREASED LIGATING FORCE

(76) Inventor: John I. Shipp, 329 W. Lincoln St., Tullahoma, TN (US) 37388

(*) Notice: Subject to any disclaimer, the term of this patent is extended or adjusted under 35 U.S.C. 154(b) by 0 days.

(21) Appl. No.: 09/259,999

(22) Filed: Mar. 1, 1999

(51) Int. Cl.[7] .................................................. B24B 1/00
(52) U.S. Cl. ............................................... 451/28; 451/56
(58) Field of Search ................................. 451/28, 56, 36, 451/38, 75, 66, 364, 365; 606/142, 158, 157, 120

(56) References Cited

U.S. PATENT DOCUMENTS

| | | | |
|---|---|---|---|
| 3,270,745 | 9/1966 | Wood | 128/325 |
| 3,439,522 | 4/1969 | Wood | 72/410 |
| 3,439,523 | 4/1969 | Wood | 72/410 |
| 4,146,130 | 3/1979 | Samuels et al. | 206/340 |
| 4,449,530 | 5/1984 | Bendel et al. | 128/325 |
| 4,450,839 | 5/1984 | Transue | 128/325 |
| 4,450,840 | 5/1984 | Mericle et al. | 128/325 |
| 4,509,518 | 4/1985 | McGarry et al. | 128/325 |
| 4,624,254 | 11/1986 | McGarry et al. | 128/325 |
| 4,799,481 | 1/1989 | Transue et al. | 128/325 |
| 4,976,722 | 12/1990 | Failla | 606/157 |
| 4,979,950 | 12/1990 | Transue et al. | 606/158 |
| 5,171,250 | 12/1992 | Yoon | 606/142 |
| 5,192,288 | 3/1993 | Thompson et al. | 606/143 |
| 5,487,746 | 1/1996 | Yu et al. | 606/151 |
| 5,501,693 | 3/1996 | Gravener | 606/157 |
| 5,509,920 | 4/1996 | Phillips et al. | 606/157 |
| 5,593,414 | 1/1997 | Shipp et al. | 606/142 |
| 5,601,573 | 2/1997 | Fogelberg et al. | 606/143 |
| 5,620,452 | 4/1997 | Yoon | 606/151 |
| 5,653,720 | 8/1997 | Johnson et al. | 606/151 |
| 5,695,502 | 12/1997 | Pier et al. | 606/143 |

OTHER PUBLICATIONS

Papainoannou, Thanassis, M.S., Daykhovsky, Leon, M.D., Grundfest, Warren S., M.D.: "Safety Evaluation of Laparoscopically Applied Clips": *Journal of Laparoendoscopic Surgery* 1996: 6(2):99–106.

Nelson, Tomothy M., M.D., Nakashima, Masanobu, M.D., Mulvihill, Sean J., M.D.: "How Secure Are Laparoscopically Placed Clips? An In Vitro and In Vivo Study": *Arch Surg.* 1992: 127:718–720: pub. Dec. 8, 1991.

Arnaud, Jean–Pierre, M.D., Bergamaschi, Roberto, M.D.,: "Migration and Slipping of Metal Clips After Celioscopic Cholecystectomy": *Surgical Laparoscopy & Endoscopy* 1993: 3(6): 487–488: pub. 1993 Raven Press, Ltd., New York.

Klein, R.D., Jessup, G., Ahari, F., Connolly, R.J., Schwaitzberg, S.D.: "Comparison of titanium and absorbable polymeric surgical clips for use in laparoscopic cholecystectomy": *Surgical Endoscopy* 1994: pub. 1994 Springer–Verlag New York Inc.

*Primary Examiner*—Derris H. Banks
(74) *Attorney, Agent, or Firm*—Waddey & Patterson; Lucian Wayne Beavers (57) ABSTRACT

A process is provided for surface treatment of surgical operating instruments so as to provide an extremely effective gripping surface of the instrument which very effectively grips a patient's tissue. Particularly the process is applicable to surgical ligation clips and clip appliers, which are used to ligate a blood vessel or the like. Operating instruments such as ligating clips and clip applicators produced with the process are also disclosed.

19 Claims, 8 Drawing Sheets

Un-treated 4000x

FIG. 10

Treated 4000x

SURGICAL LIGATION CLIP WITH INCREASED LIGATING FORCE

BACKGROUND OF THE INVENTION

1. Field of the Invention

The present invention relates generally to the field of ligation clips for surgical procedures, and more particularly, but not by way of limitation, to relatively small clips which are adapted for use in laparoscopic surgery.

2. Description of the Prior Art

There are many designs for surgical clips included in the prior art, some of which are particularly adapted for use in laparoscopic surgery. For example, U.S. Pat. No. 5,593,414 to Shipp, et al., which is assigned to the assignee of the present invention, discloses one form of surgical ligation clip to which the present invention can be applied. It has also been recognized that there are sometimes problems with surgical ligation clips slipping off of the blood vessel or other member to which they are clipped, and it is suggested in U.S. Pat. 5,593,414 that the gripping force of the clip can be enhanced by use of ridges, notches, or various other treatments to the clamping surfaces thereof U.S. Pat. No. 5,620,452 discloses a surgical clip with penetrating members to prevent the clip from slipping off of the vessel.

U.S. Pat. No. 5,487,746 discloses a surgical clip having openings through which a portion of the clamped tissue will protrude.

U.S. Pat. No. 4,799,481 discloses a clip with tissue gripping grooves. These grooves offer some increase in removal force. Additionally the grooves substantially complicate the manufacturing process of such clips.

U.S. Pat. No. 5,601,573 discloses a clip having a surface characterized by a series of cross-hatches or dimples 97 as seen in FIG. 12.

U.S. Pat. Nos. 4,624,254 and 4,509,518 shows at FIGS. 35–40 a clip surface characterized by a series of longitudinal slots.

U.S. Pat. No. 4,799,481 shows a clip surface characterized by a series of cross hatches.

Tests on such clips as those of U.S. Pat. NoS. 4,624,254 and 4,799,481 are reported in *Journal of Laparoendoscopic Surgery*, Vol. 6, No. 2, 1996, p.99, and in *Arch. Surgery*, Vol. 127, June 1992, p.718.

U.S. Pat. No. 5,695,502 shown in FIGS. 7A–7C a clip having grooves or teeth 106.

U.S. Pat. No. 5,509,920 discloses a clip having complementary bumps and recesses to grip a vessel.

U.S. Pat. No. 5,501,693 discloses a clip having a complementary rib and groove for gripping.

U.S. Pat. No. 4,450,840 discloses at col. 4, 1.50–55 the use of ridges or grooves on a clip. Similar disclosure is found in U.S. Pat. No. 4,450,839 at col. 4, 1.47–50.

U.S. Pat. No. 4,449,530 discloses a clip having a diamond pattern 16 to improve gripping.

U.S. Pat. No. 4,976,722 discloses a clip having complementary protrusions and recesses for gripping.

U.S. Pat. No. 4,979,950 discloses a clip having a pattern of grooves for gripping tissue.

The following two articles discuss problems of clip slippage:

Arnaud, et al., "Migration and Slipping of Metal Clips After Celioscopic Cholecystectomy, *Surg. Laparoscope & Endoscopy:* Vol. 3, No. 6, pp. 487–88 (1993); and Klein, et al., "Comparison of titanium and absorbable polymeric surgical clips for use in laparoscopic cholecystetomy", *Surg. Endoscopy*, Vol. 6, pp. 753–758 (1994).

The following patent references show other clip constructions, most of which have grooves or the like on the clips:

U.S. Pat. No. 3,439,523;
U.S. Pat. No. 3,270,745;
U.S. Pat. No. 3,439,522;
U.S. Pat. No. 4,146,130;
U.S. Pat. No. 5,171,250; and
U.S. Pat. No. 5,192,288.

Thus it is seen that there is a need for improved techniques for treatment of the surface of ligation clips and other surgical instruments which are intended to grip blood vessels or the like, so as to reduce the incidence of clips slipping out of place.

The present invention provides such a surface treatment which can be applied to spring clips like those of U.S. Pat. No. 5,593,414 or to other surgical instruments. Also provided are preferred constructions for such spring clips and surgical instruments.

SUMMARY OF THE INVENTION

A method of treatment of the surface of the surgical instrument is provided which includes steps of blasting the surface with a stream of particles and thereby roughening the surface so that the surface will more effectively grip human tissue than would an untreated surface.

In a preferred method, the particles are white aluminum oxide having a grit size in the range from about 100 to about 180, and preferably with a grit size of about 150.

When such a treatment is provided to a titanium drawn wire clip for approximately two seconds, dramatic changes are created in the surface texture of the clip.

Prior to treatment the drawn wire clip has a surface topography defined by regular dimpled surface features and occasional smeared metal plateaus, all of which has a directional characteristic generally parallel to the length of the wire. After the preferred treatment, the surface topography of the treated metal wire clip is free of such smooth metal plateaus and regular dimpled surface features. Instead, the operative treated surface of the clip has a surface topography characterized by irregular multi-faceted jagged surface features having dimensions on the order of 1 to 10 microns.

Standard tests show that this treatment increases the coefficient of friction of a spring type ligation clip on material that is typically used to simulate body vessels in clip removal tests from a value of approximately 0.25 for the untreated clip up to a value in the range of 0.65 to 0.71 for a clip which has received the most preferred surface treatment.

Preferred processes are disclosed for treating the surface of various surgical instruments including ligation clips.

Also disclosed are improved surgical instruments and ligation clips having such treated surfaces.

It is therefore an object of the present invention to provide improved surgical instruments having surfaces which may more securely grip a ligated blood vessel or the like.

Another object of the present invention is the provision processes for manufacturing such surgical instruments.

Still another object of the present invention is the provision of an improved ligation clip which is less likely to slip off of a ligated vessel.

Numerous other objects features and advantages of the present invention will be readily apparent to those skilled in the art upon the reading of the following disclosure when taken in conjunction with the accompanying drawings.

DETAILED DESCRIPTION OF THE PREFERRED EMBODIMENTS

As noted above in the description of the prior art there have been a number of surgical ligation clips which have included various means for attempting to increase the removal force on the clips. To date, such clips have been inadequate.

Among the most demanding uses for surgical ligation clips is the ligation of an artery in a patient with very high blood pressure, for example 300 mm of Hg systolic pressure. The ligation force required to totally occlude such a vessel is on the order of 100 grams. Although most ligation clips of the prior art will readily supply that magnitude of ligation force, if they are properly applied, additional problems have arisen in connection with the development of laparoscopic surgery. With the advent of laparoscopic surgery, a more stringent requirement arose for ligation clips. Many of these type procedures are performed as same day surgery, and since there is much less discomfort to the patient, rather stringent physical activity often occurs early in the healing process. This activity can dislodge a clip of the prior art with disastrous or near disastrous results. Thus while many prior art clips which were satisfactory in the case of open surgical procedures, where hospital stays are much longer and the body's natural healing process seals the vessel while the patient is relatively immobile, those same clips may not be satisfactory for laparoscopic surgery. Ligation clips used in laparoscopic surgery are under forces, not only from vessel pressure, but from the physical impulses or jarring generated by patient's physical activity of moving around.

Thus the present invention has been developed to provide ligation clips which increase the forces required to remove the ligation clip from the vessel in both directions, perpendicular and parallel to the axis of the vessel.

It is also noted that the surgical ligation clip of the present invention provides this increased holding force without causing significant trauma to the vessel as is the case in some prior art devices such as U.S. Pat. No. 5,620,452 wherein penetrating members are used to anchor the clip to the vessel.

One form of spring clip to which the surface treatment of the present invention may be applied is that shown in U.S. Pat. No. 5,593,414 to Shipp, et al., assigned to the assignee of the present invention, the details of which are incorporated herein by reference.

Figure 1:
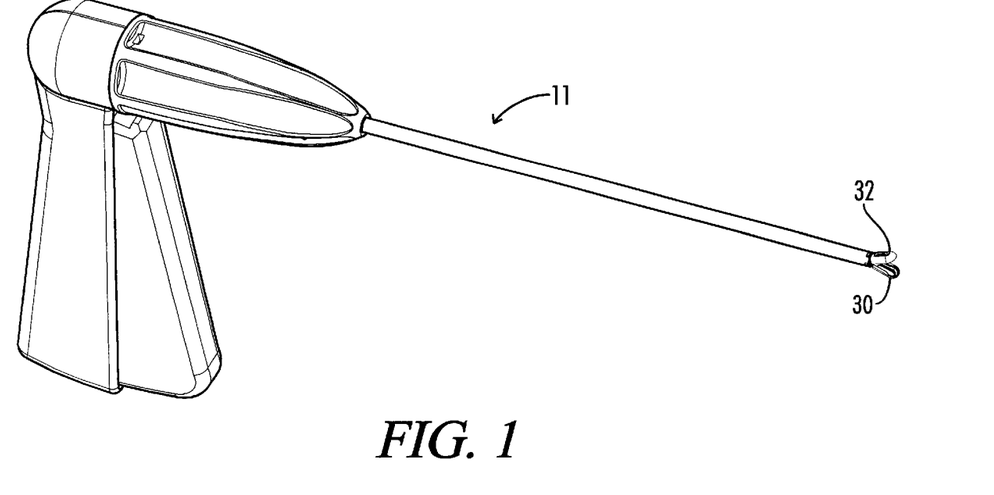
FIG. 1 is a perspective view of a clip applicator gun which is one form of surgical instrument to which the present invention may be applied.
Figure 3:
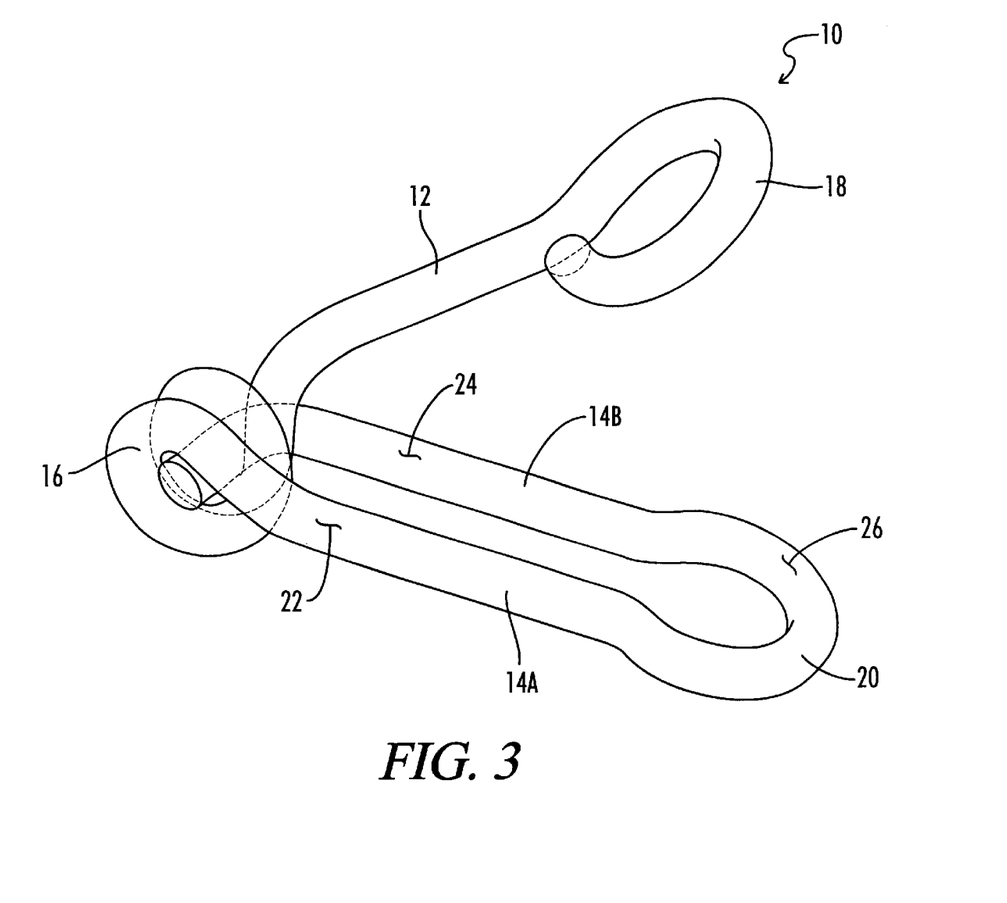
FIG. 3 is an isometric view of a drawn wire ligation clip of the type which would be applied by the clip applicator of FIG. 1. The surface treatment of the present invention can be applied to the clamping arms of a drawn wire clip like that of FIG. 3.

Another more preferred clip is the clip 10 which is illustrated in FIG. 3, and which is applied with a clip applicator 11 like that illustrated in FIG. 1. The details of construction of the clip 10, other than the surface treatment which is the subject of the present invention, and the details of construction of the clip applicator 11 are set forth in more detail in U.S. patent application Ser. No. 09/258,943 filed concurrently herewith entitled "Ligation Clip And Clip Applier" by Shipp, et al. and assigned to the assignee of the present invention, the details of which are incorporated herein by reference.

The spring clip 10 includes a first arm 12 and a second arm 14. A coil spring portion 16 joins the first and second arms 12 and 14 to bias the arms 12 and 14 toward a closed position. A first wire loop 18 is defined upon the end of first arm 12, and a second wire loop 20 is defined upon the end of second arm 14. It is noted that the first arm 12 is comprised of a single wire member, and the second arm 14 is comprised of two parallel arms numbers 14A and 14B.

The clip 10 is shown in an open position in FIG. 3. It would be held in such an open position by the applicator 11 when placed over the blood vessel.

Figure 4:
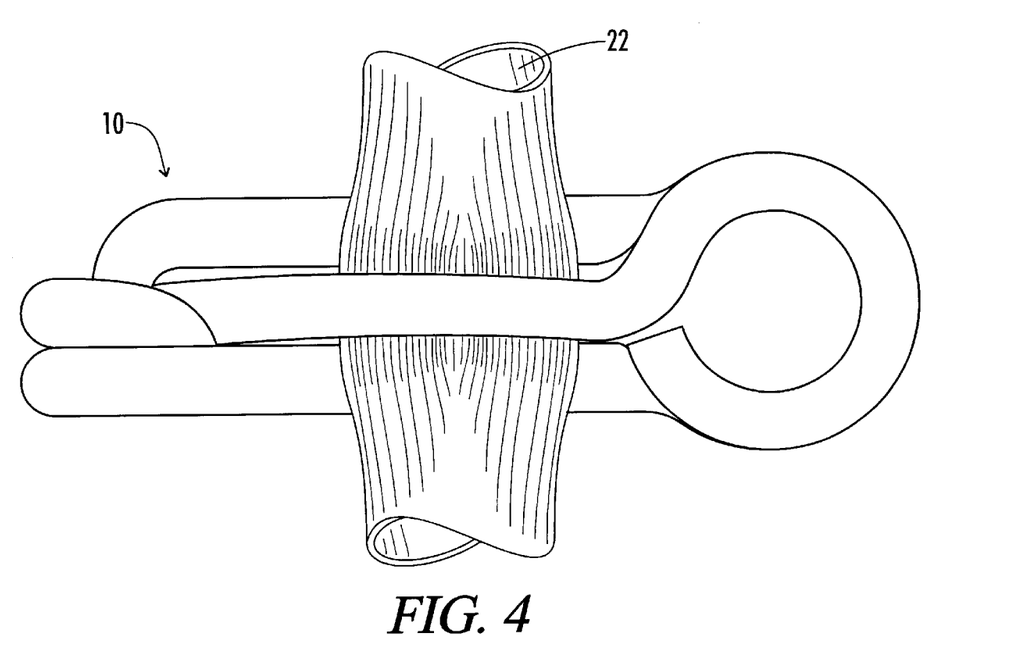
FIG. 4 is illustrates the clip of FIG. 3 in place about a blood vessel to ligate the same.
Figure 5:
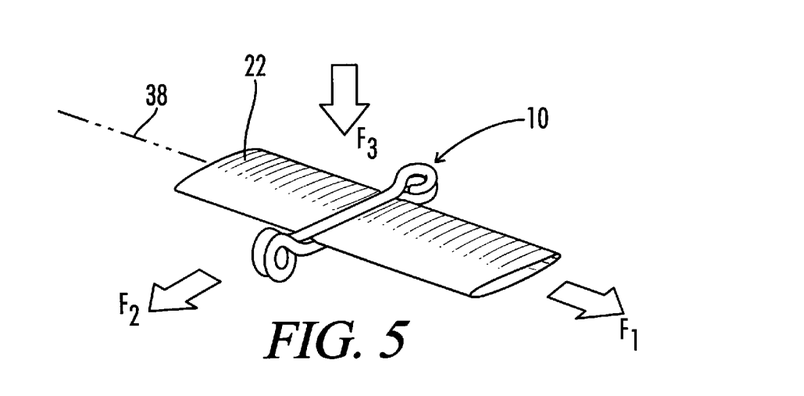
FIG. 5 is an isometric somewhat schematic representation defining the primary directions of force between the clip and blood vessel which may tend to cause the clip to slip relative to the blood vessel.

FIGS. 4 and 5 illustrate the clip 10 in a relaxed or closed position about a blood vessel or the like 22 to ligate or close the same.

Referring to FIG. 3, it will be appreciated that the vessel 22 will operatively engage certain portions of those surfaces of arm 12 and arm 14 which face toward each other. Also, with the design of the clip 10 having the loop shaped ends 18 and 20 it is possible to ligate a vessel between the loop shaped ends. Those portions of the clip 10 which are potentially to be engaged with the vessel 22 are referred to herein as the operative surfaces of the clip. For example in FIG. 3 the operative surface of first arm 12 would be the lower portions of the arm 12 and the loop 18, and the operative portions of the arm 14 would be the upper surfaces 22 and 24 of arm portions 14A and 14B, and the upper surface 26 of loop 20.

It will be appreciated that owing to the size of the ligating clips and the manner of surface treatment, substantially the entire clip may receive the sandblast treatment and thus the roughened surface is created over substantially the entire surface of the clip, including those surfaces which actually engage the blood vessel and those which do not. In other devices, such as for example, the applicator 11, it may be found to be preferable to simply spot treat a surface which is going to engage the patient's tissue, such as the surfaces 34 and 36 without subjecting the entire device to the sandblast procedure.

Figure 2:
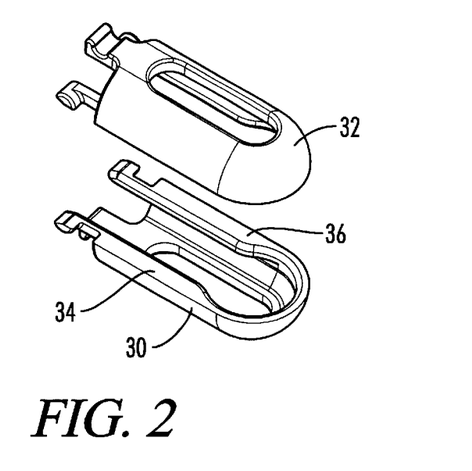
FIG. 2 is an enlarged exploded view of the clamping jaws at the operative end of the instrument of FIG. 1. These clamping jaws provide the operative surfaces to which the improved surface treatment of the present invention would be applied.

Similarly, with reference to FIGS. 1 and 2, the surface treatment of the present invention can be applied to other operating instruments such as the applicator device 11 itself. The applicator device 11 has a pair of hinged jaws 30 and 32 on its operative end. The hinged jaws are shown in an enlarged exploded view in FIG. 2.

It will be appreciated that the blood vessel 22 will be clamped between the jaws 30 and 32 and then the clip 10 will be placed over the vessel 22. It is important, however, to have a good gripping surface between the blood vessel 22 and each of the jaws 30 and 32 without causing trauma to the vessel. For example, the jaw 30 has upper surfaces 34 and 36 which complement and face similar lower surfaces (not shown) on upper jaw 32. These surfaces such as 34 and 36 may be described as the operative surfaces of the jaws 30 and 32 of applicator device 12. The surface treatment of the present invention can be applied to the operative surfaces such as 30 and 34 to allow the jaws 30 and 32 to more securely grip the blood vessel 22 during the process of applying the clip 10 to ligate the blood vessel 22.

The surface treatment described herein, and modifications thereof, may be applied to various types of structures and particularly metal structures. The clip 12 disclosed herein is preferably drawn from 0.030 diameter implantable grade titanium wire such as 6Al-4V-ELI. Also, the jaws 30 and 32 of the preferred applicator device 12 are preferably constructed of a stainless steel alloy such as 17–4.

Preferred Surface Treatments

The method of treating the operative surfaces of a surgical instrument such as clip 10 or the jaws of applicator 11 can be generally described as blasting the surface with a stream of particles and thereby roughening the surface so that the surface will more effectively grip human tissue than would a comparable untreated surface.

In the preferred embodiment the operative surface of the clip or applicator is exposed to a pressurized blast of sand or other particular material. The preferred embodiment is an approximately two second blast of 150 grit white aluminum oxide from a sandblaster under 80 PSI of pressure. More generally the blasting may be performed for a time in the range of 0.5 to 5.0 seconds. An example of the preferred aluminum oxide is WFA150 sold and distributed by Methyl Dimension of Vernon, Calif.

Other sizes of particulate material can be used and can accomplish the purposes of the present invention to a degree, but it has been determined that this particular 150 grit material provides superior results. Table 1 set forth below shows a comparison of the resulting gripping effectiveness of clips in the untreated condition and then treated with the process of the present invention using various grit sizes. The column headed "Untreated" shows the results for 10 samples of untreated clips. The three remaining columns show the test results for 10 samples using 100 grit, 150 grit, and 180 grit, respectively.

TABLE I

"COEFFICIENT OF FRICTION IN STANDARDIZED TESTS"

| Sample No. | Untreated | 100 grit | 150 grit | 180 grit |
| --- | --- | --- | --- | --- |
| 1 | 0.26 | 0.56 | 0.66 | 0.53 |
| 2 | 0.28 | 0.53 | 0.69 | 0.52 |
| 3 | 0.26 | 0.5 | 0.71 | 0.57 |
| 4 | 0.27 | 0.54 | 0.69 | 0.56 |
| 5 | 0.29 | 0.55 | 0.65 | 0.51 |
| 6 | 0.25 | 0.55 | 0.67 | 0.59 |
| 7 | 0.25 | 0.57 | 0.69 | 0.60 |
| 8 | 0.27 | 0.49 | 0.7 | 0.53 |
| 9 | 0.28 | 0.56 | 0.67 | 0.56 |
| 10 | 0.25 | 0.52 | 0.65 | 0.54 |
| Average | 0.266 | 0.537 | 0.68 | 0.551 |

The test procedure to determine the gripping effectiveness as set forth in Table I comprised placement of the clip in a ligating position similar to that shown in FIG. 3 about a length of silicone tubing which provides a uniform representative model of the gripping forces between the clip and a human blood vessel. The tubing utilized in these tests was Manosil brand silicone tubing having a $\frac{1}{30}^{th}$ inch inside diameter and a $\frac{1}{30}^{th}$ inch wall thickness. The numbers set forth in Table I represent the ratio of the force required to pull the clip off of the tubing in a direction such as that represented by a $F_2$ in FIG. 5 perpendicular to the center line 38 of the tubing, to the normal force exerted by the clip against the surface of the vessel 22. Thus the numbers of Table I effectively represent a coefficient of friction between the surface of the clip and the silicone tubing which represents the blood vessel 22.

As is apparent from Table I, the results within each group of tests are very consistent. The tests for the untreated clips showed a coefficient of friction ranging from 0.25 to 0.29, with the average for the ten tests being 0.266.

The group of clips treated with 100 grit particulate material showed a ranged of coefficient of friction from 0.49 to 0.57 with an average of 0.537.

The group of clips treated with the preferred 150 grit material showed a range from 0.65 to 0.71 with and average of 0.68.

The group of clips treated with 180 grit particulate material showed a coefficient of friction having a range of 0.51 to 0.6 with an average of 0.551.

Thus it is apparent from the text results shown in Table 1 that there is, in fact, a preferred particulate material for forming the treated surfaces of the present invention. It is apparent that use of the 100 grit and 180 grit sizes both produced results that were substantially improved as compared to the untreated surface, but which were significantly less effective than the results from the 150 grit material.

Although separate test data have not been presented, it will be readily apparent that the treated clips of the present invention will also have improved coefficient of friction and thus improved resistance to dislodgement relative to the blood vessel 22 in the direction $F_1$ parallel to the center line 38 of blood vessel 22.

Although the preferred time of exposure of the clip to the sandblast procedure is approximately two seconds, experience has shown that blasting times in the range of 0.5 to 5.0 seconds should provide reasonably effective results.

The method represented by the tests of Table I can be characterized as roughening the operative surface of the clip such that a coefficient of friction between the roughened surface and the described silicone test piece is greater than 0.5, and more preferably at least 0.65. This is sharply contrasted to the untreated clip which has a coefficient of friction of only about 0.266.

Figure 6:
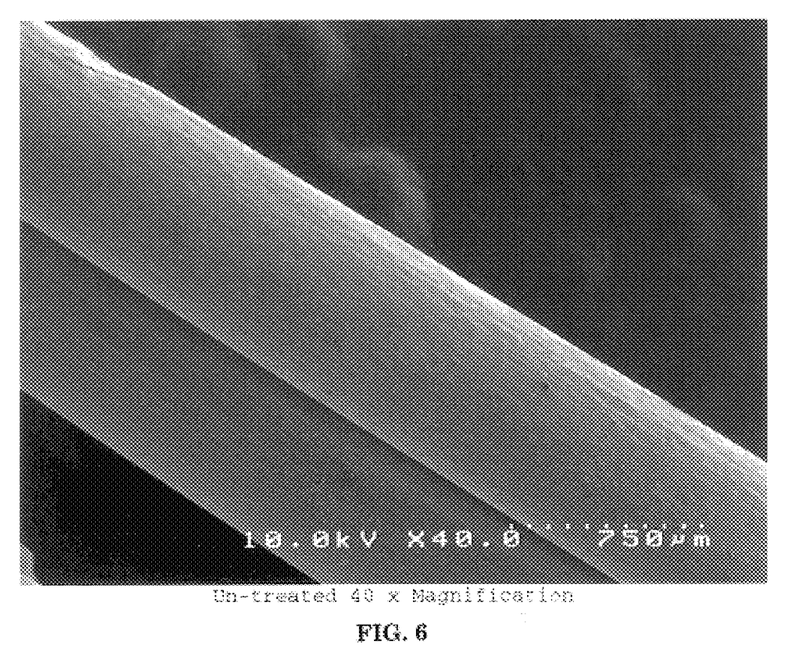
FIG. 6 is a photograph of an untreated clip like that of FIG. 3 taken with an electron microscope at a magnification of 40×.
Figure 15:
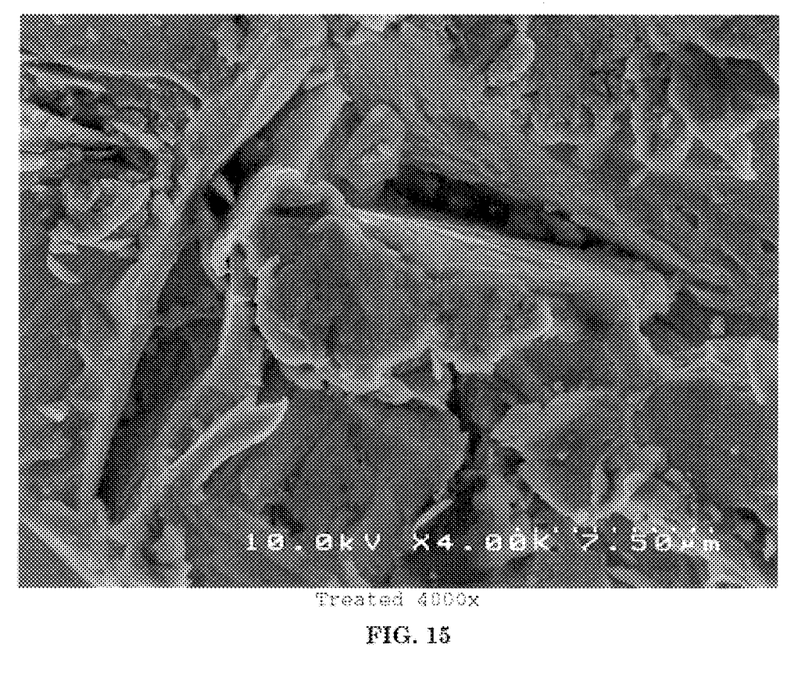

Turning now to the electron microscope photographs of the various test pieces as set forth in FIGS. 6 and 15, the results of this surface treatment and the reason for its effectiveness can be dramatically seen and further described.

Figure 7:
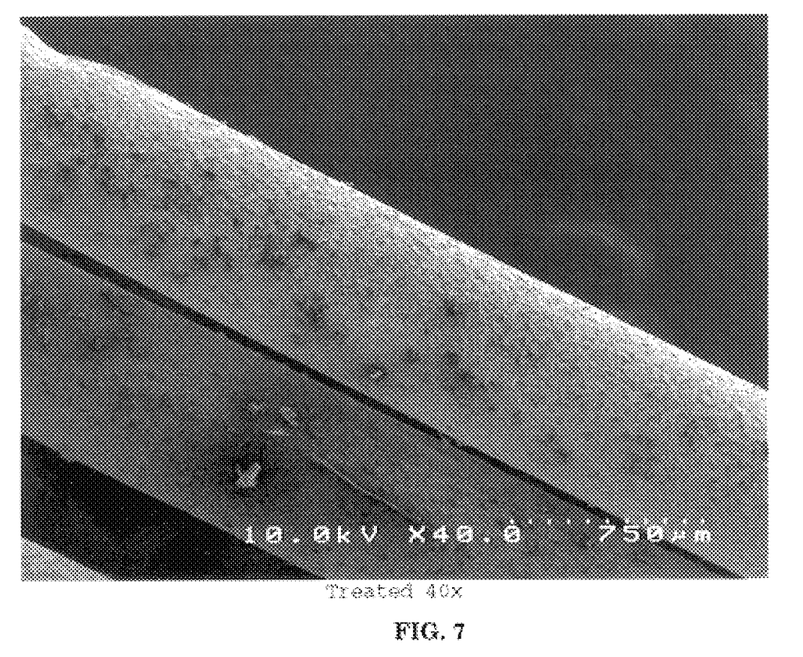
FIG. 7 is a photograph of a treated clip at a magnification of 40×.

FIGS. 6 and 7 show side by side the untreated clip in FIG. 6 and the treated clip in FIG. 7, both at a magnification of 40×.

In FIGS. 6 and 7 the magnification is not yet great enough to clearly show the resulting surface features, although it is readily apparent that the outer surface of the untreated surface of FIG. 6, appears substantially smoother than that of the treated clip in FIG. 7.

Figure 8:
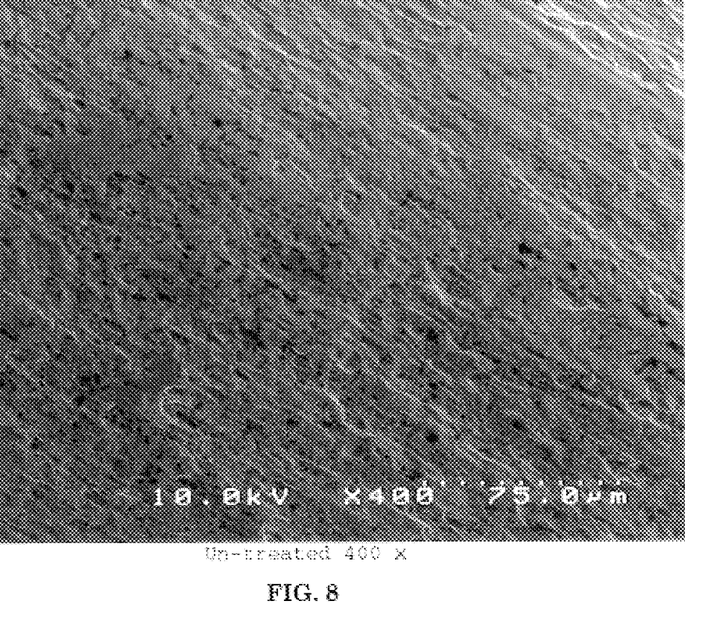
FIG. 8 is a photograph of an untreated clip at a magnification of 400×.
Figure 9:
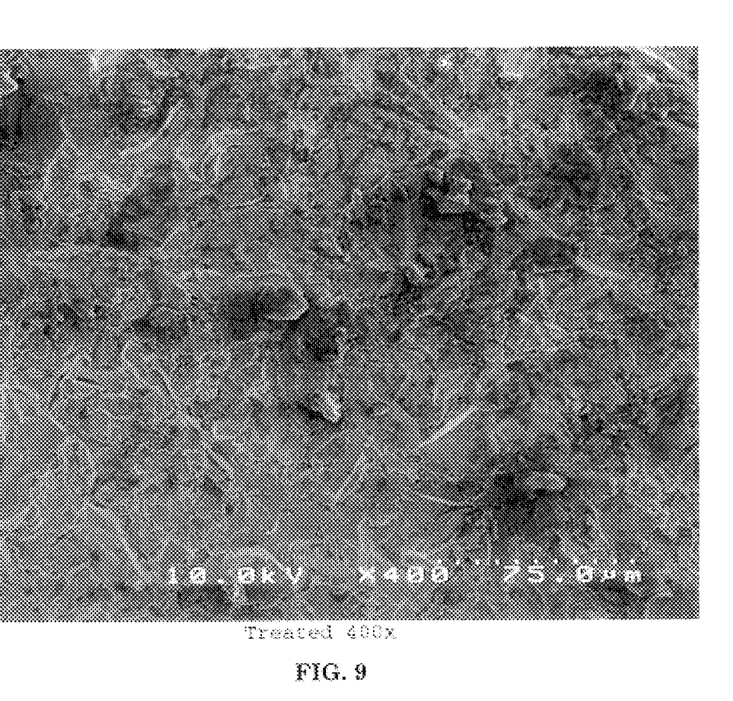
FIG. 9 is a photograph of a treated clip at a magnification of 400×.

The distinction between the untreated and treated surface becomes more apparent at a 400× magnification as can be seen by comparing FIGS. 8 and 9. Again FIG. 8 is the untreated surface at 400× magnification and FIG. 9 is the treated surface at 400× magnification.

It is noted that the photographic FIGS. 6 through 15 all have a scale displayed thereon in the lower right corner. A series of ten dots are shown and below the line of dots is the scale corresponding to the line of ten dots. Thus in FIGS. 8 and 9, the ten dots represent a length of 75 microns. As is apparent if FIGS. 8 and 9, the untreated surface has a regular pitted or dimpled appearance which clearly has a directional element which is parallel to the length of the wire as would be expected for drawn wire wherein the surface results from pulling the same in a linear motion through a circular die. It can be seen in FIG. 9 that the treated surface has lost this regular feature and has a much more irregular jagged surface topography.

Figure 10:
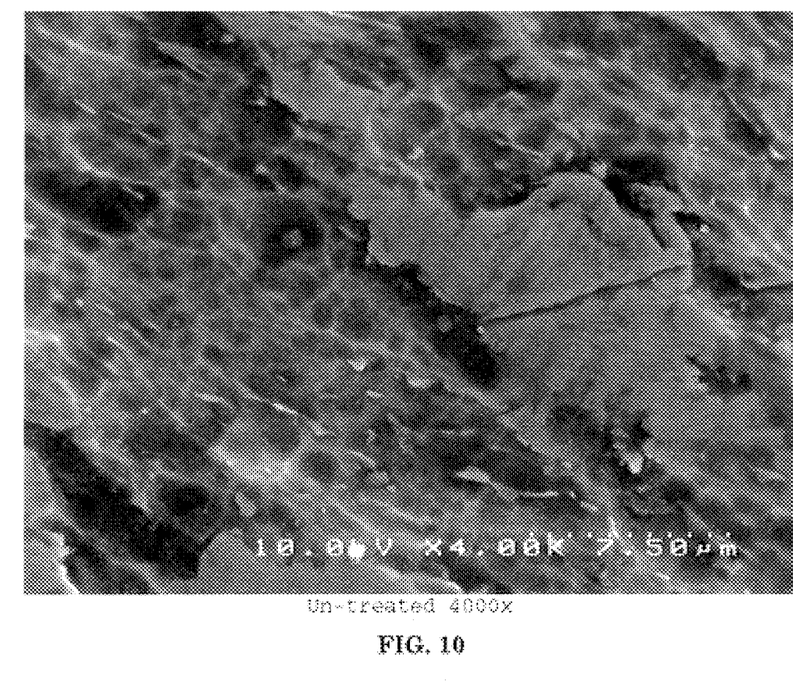
FIG. 10 is a photograph of an untreated clip at a magnification of 4000×.
Figure 11:
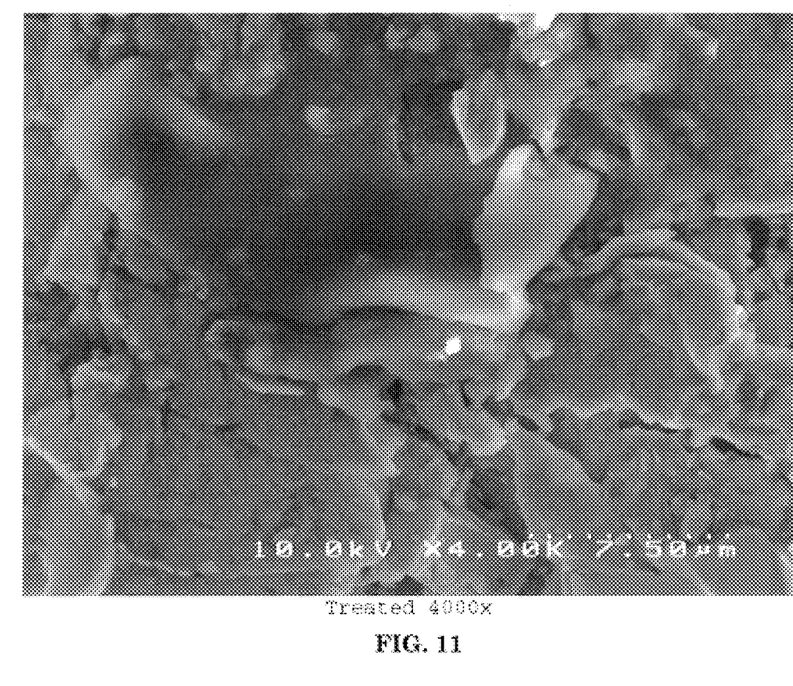
FIG. 11 is a photograph of a treated clip at a magnification of 4000×.

This distinction is best seen in the 4000× magnification photographs of FIGS. 10 and 11.

In FIG. 10, the untreated surface is shown to be comprised of areas of somewhat regular pitted or dimpled texture with islands of plateau like nature of smeared metal. This again is what one would expect from the wire being drawn through a die, and the points of actual contact between the surface of the wire and the die result in the smeared metal tops of the plateaus.

As seen in FIG. 11, again the treated surface is very irregular and is made of multi-faceted jagged surface features.

In order to show the representative nature of FIGS. 10 and 11, additional photographs are provided of both the treated and untreated surface at different locations at 4000× magnification.

Figure 12:
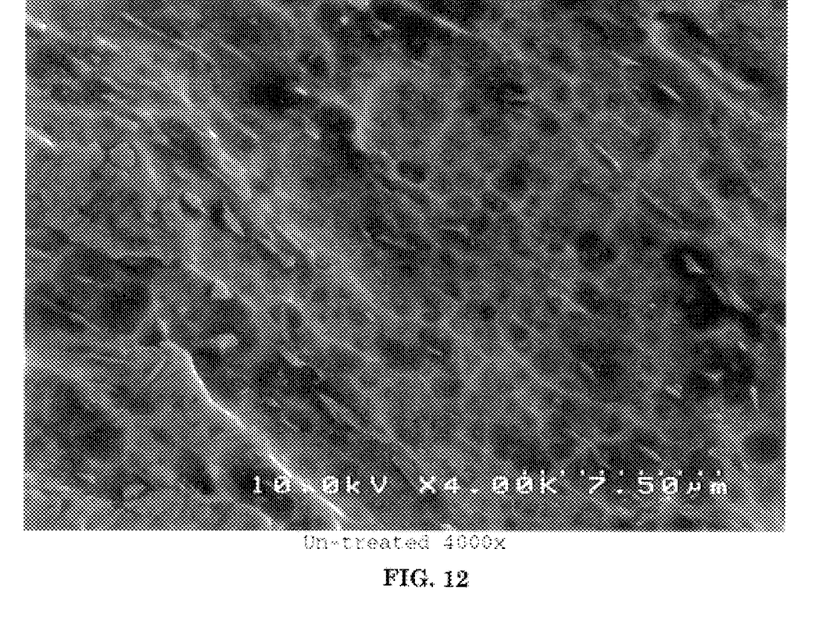
FIGS. 12 and 13 are two additional photographs of an untreated clip at a magnification of 4000× taken at various locations upon the clip so that FIGS. 10, 12, and 13 provide several representative views at 4000× of the untreated clip.
Figure 13:
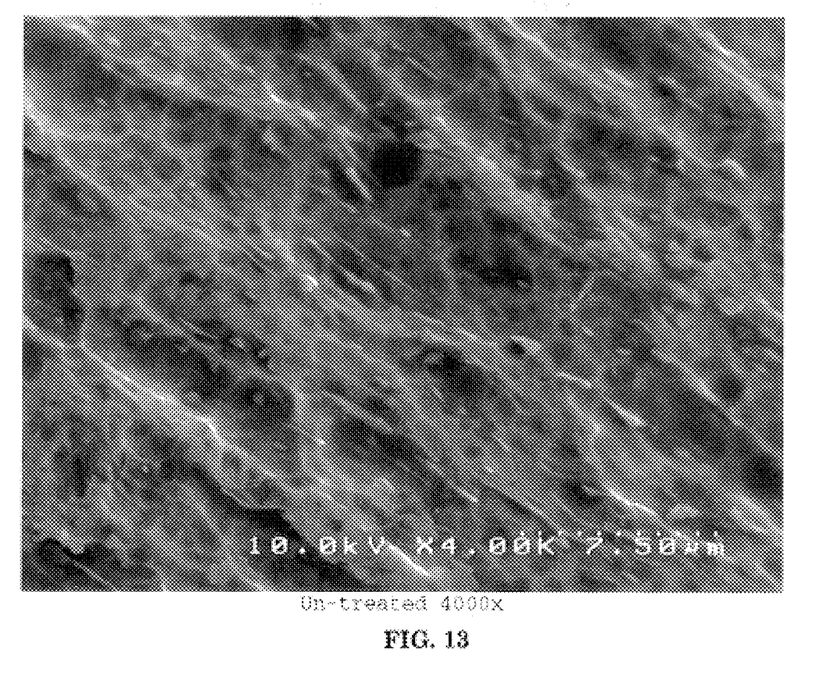

FIGS. 12 and 13 are two additional photographs at different locations upon the same untreated wire clip which continue to show the rather regular pitted surface having a directional characteristic and having islands of plateau like smeared metal features.

Figure 14:
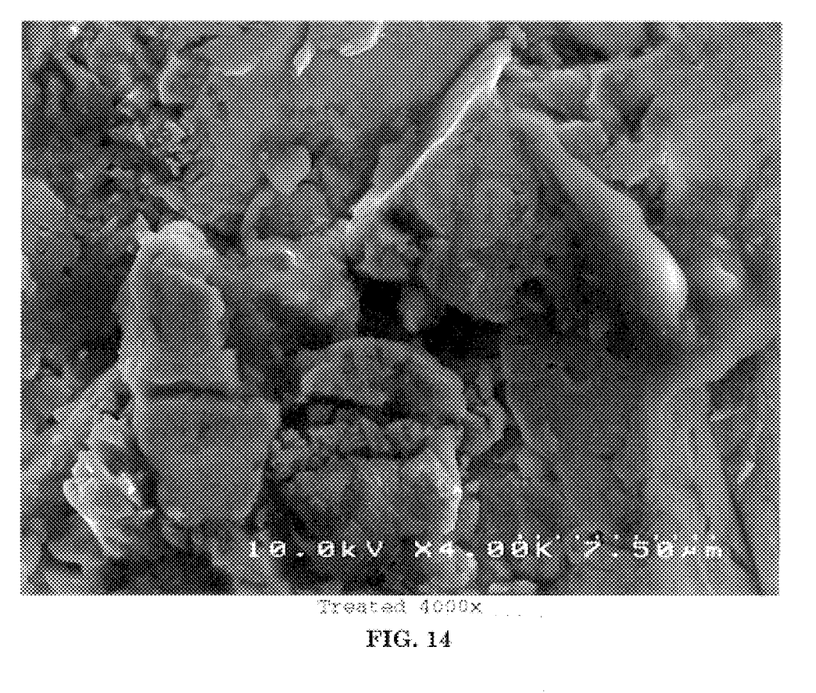
FIGS. 14 and 15 provide two additional views at a magnification 4000× of the treated clip at various locations on that clip. Thus FIGS. 11, 14, and 15 provide several representative views taken at various locations of one treated clip at magnification 4000×.

FIGS. 14 and 15, on the other hand, are two additional 4000× magnification photographs of the treated surface and here the multi-faceted irregular surface topography of the preferred treated surface is most clearly visible. As is apparent from a comparison of these surface features to the scale set forth in the lower right corner of FIGS. 11, 14, and 15, it can be seen that these multi-faceted surface features have dimensions generally on the order of one to ten microns, with some of the longer dimensions being up to and sometimes above ten microns. It is apparent that these jagged surface features are random and irregular and result in a multitude of microscopic sharp points, hooks, crags, protrusions, and the like. It will be readily apparent that this very jagged sharp irregular surface texture will provide a vastly superior gripping motion when the treated surface of the clip 10 is used to grip a soft ductile material such as a human blood vessel or the standard silicone tube used in the tests of Table 1. It will be appreciated that the jagged irregular surfaces are of such dimensions that they will not puncture through the vessel wall, however.

Additional comparative data showing the superior performance of a ligation clip treated by the surface treatment procedure of the present invention as compared to several other prior art devices presently on the market is shown on the following Table II.

TABLE II

"PERFORMANCE COMPARISON"

| Clip | Mean Dislodgment Force. Grams | Source of Info. |
|---|---|---|
| Transverse Clip Security in Vitro | | |
| Ethicon, 5mm* | 206 +/− 3.2% | (Ref. 3) |
| Endo Clip II* | 266 | (Ref. 1) |
| | 185 +/− 3.9% | (Ref. 2) |
| Ligaclip ERAC** | 239 | (Ref. 1) |
| | 273 +/− 1.5% | (Ref. 2) |
| Present Invention | 566 +/− 1.5% | (Ref. 3) |
| Axial Clip Security in Vitro | | |
| Ethicon, 5 mm* | 279 +/− 3% | (Ref. 3) |
| Endo Clip II* | 488 +/− 3.7% | (Ref. 2) |
| Ligaclip ERAC** | 416 +/− 4.9% | (Ref. 2) |
| Present Invention | 813 +/− 1.1% | (Ref. 3) |
| * Manufactured by Ethicon, Inc. | | |
| ** Manufactured by U.S. Surgical Corp | | |

References:
1. Journal of Laparoendoscopic Surgery, Vol. 6, No. 2, 1996. p. 99. Measurements made using 2.4 mm Silicone tubing. N = 24
2. Arch Surg., Vol. 127, June 1992. p. 718. Measurements made using 2.4 mm Silicone tubing. N = 36
3. Unpublished measurements using 2.4 mm Silicone tubing. N = 40

The Ethicon 5 mm clip has a construction as shown in European Patent Application number 95301328.1 having a surface characterized by a series of cross hatches. The Endo Clip II is of the type shown in U.S. Pat. No. 4,624,254 and has a clip surface characterized by a series of longitudinal slots.

The Ligaclip ERAC is of the type shown in U.S. Pat. No. 4,799,481 and has a clip surface characterized by a series of cross hatches.

The test data on the Endo Clip II and the Ligaclip ERAC are taken from the referenced publications. The techniques utilized to generate the data disclosed in reference 1, were performed as described in Journal of Laparoendoscopic Surgery, Volume 6, No. 2, 1996, pages 99–106, the details of which are incorporated herein by reference. The data for reference 2 was obtained as described in reference 2, Arch Surgery, Volume 127, June 1992, pages 718–720, the details of which are incorporated herein by reference.

The additional data developed by applicants and noted by reference 3 was developed by using techniques similar to those of references 1 and 2. More particularly, the test procedure utilized to generate the additional data of reference 3, Table II was conducted in accordance with the procedures as described in reference 1 and 2.

Thus the present invention provides improved processes for treating the surfaces of operating instruments, and provides improved operating instruments such as ligating clips and clip applicators which are produced through the use of this process.

While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the attended claims.

What is claimed:

1. A method of treating the surface of a surgical implement comprising:
   (a) blasting the surface with a stream of particles; and
   (b) thereby roughening the surface so that the surface will more effectively grip human tissue than would an untreated surface; and
   wherein in step (a) the particles are aluminum oxide having a grit size in a range of from about 100 to about 180.

2. The method of claim 1, wherein:
   in step (a) the particles have a grit size of about 150.

3. The method of claim 1, wherein the blasting is performed for a time in the range of 0.5 to 5.0 seconds.

4. A method of treating the surface of a surgical implement comprising:
   (a) blasting the surface with a stream of particles; and
   (b) thereby roughening the surface so that the surface will more effectively grip human tissue than would an untreated surface; and
   wherein step (b) is further characterized as roughening the surface such that a coefficient of friction between the roughened surface and a silicone test piece is greater than 0.5.

5. The method of claim 4, wherein step (b) is further characterized in that the roughened surface has irregular multi-faceted jagged surface features.

6. The method of claim 5, wherein some of the irregular multi-faceted jagged surface features have major dimensions of up to and greater than 10 microns.

7. A method of treating the surface of a surgical implement comprising:
   (a) blasting the surface with a stream of particles: and
   (b) thereby roughening the surface so that the surface will more effectively grip human tissue than would an untreated surface; and
   wherein the blasting is performed for a time in the range of 0.5 to 5 seconds.

8. A method of treating the surface of a surgical implement comprising:
   (a) blasting the surface with a stream of particles; and
   (b) thereby roughening the surface so that the surface will more effectively grip human tissue than would an untreated surface; and
   wherein step (b) is further characterized as roughening the surface such that a coefficient of friction between the roughened surface and a silicone test piece is greater than 0.5.

9. A method of treating the surface of a surgical implement comprising:
   (a) blasting the surface with a stream of particles: and
   (b) thereby roughening the surface so that the surface will more effectively grip human tissue than would an untreated surface; and
   wherein step (b) is further characterized as roughening the surface such that a coefficient of friction between the roughened surface and a silicone test piece is greater than 0.65.

10. A method of treating the surface of a surgical implement comprising:
    (a) blasting the surface with a stream of particles; and
    (b) thereby roughening the surface so that the surface will more effectively grip human tissue than would an untreated surface; and
    wherein step (b) is further characterized in that the roughened surface has irregular multi-faceted jagged surface features.

11. The method of claim 10, wherein some of the irregular multi-faceted jagged surface features have major dimensions of up to and greater than 10 microns.

12. A method of treating the surface of a surgical implement comprising:
    (a) blasting the surface with a stream of particles; and
    (b) thereby roughening the surface so that the surface will more effectively grip human tissue than would an untreated surface; and
    wherein in step (a) the surgical instrument is a clip for ligating a blood vessel.

13. A surgical ligation clip produced by the process of treating the surface of the surgical ligation clip by the method of:
    (a) blasting the surface with a stream of particles; and
    (b) thereby roughening the surface so that the surface will more effectively grip human tissue than would an untreated surface.

14. A surgical instrument having an operative area designed to grip a patient's tissue, the operative area having a roughened surface with irregular multi-faceted jagged surface features, wherein some of the irregular multi-faceted jagged surface features have major dimensions of up to and greater than 10 microns.

15. The instrument of claim 14, wherein the instrument is a surgical ligation clip.

16. A surgical ligation clip comprising:
    first and second arms;
    a spring portion biasing the first and second arms towards each other to ligate a patient's tissue there between; and
    the first and second arms having first and second roughened surfaces respectively, arranged to clamp the patient's tissue there between, the clip having a coefficient of friction between the roughened surfaces and a cylindrical silicone tubing of $\frac{1}{30}$ inch inside diameter and $\frac{1}{30}$ inch wall thickness such that a force required to pull the clip off of the tubing perpendicular to the centerline of the tubing exceeds 0.5 times the force exerted by the clip upon the tubing normal to the tubing.

17. The clip of claim 16, wherein the roughened surfaces have irregular multi-faceted jagged surface features.

18. The clip of claim 17, wherein some of the irregular multi-faceted jagged surface features have major dimensions of up to 10 microns and greater.

19. The clip of claim 16, wherein the force required to pull the clip off of the tubing perpendicular to the centerline of the tubing exceeds 0.65 times the force exerted by the clip normal to the tubing.

* * * * *